(12) United States Patent
Siccardi et al.

(10) Patent No.: US 11,707,287 B2
(45) Date of Patent: Jul. 25, 2023

(54) DISPOSABLE GUIDE DEVICE FOR SPINAL SURGERY

(71) Applicant: MEDACTA INTERNATIONAL SA, Castel San Pietro (CH)

(72) Inventors: Francesco Siccardi, Castel San Pietro (CH); Meinrad Fiechter, Castel San Pietro (CH); Alberto Lipari, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 42 days.

(21) Appl. No.: 17/357,612

(22) Filed: Jun. 24, 2021

(65) Prior Publication Data

US 2021/0393273 A1    Dec. 23, 2021

Related U.S. Application Data

(63) Continuation of application No. 16/333,055, filed as application No. PCT/IB2017/055688 on Sep. 20, 2017, now Pat. No. 11,058,443.

(30) Foreign Application Priority Data

Sep. 23, 2016 (IT) .................. 102016000095900

(51) Int. Cl.
*A61B 17/17* (2006.01)
*A61B 17/90* (2006.01)
(Continued)

(52) U.S. Cl.
CPC ...... *A61B 17/1757* (2013.01); *A61B 17/7074* (2013.01); *A61B 17/848* (2013.01);
(Continued)

(58) Field of Classification Search
CPC ..... A61B 17/15; A61B 17/17; A61B 17/1739; A61B 17/1757; A61B 2017/568; A61B 17/7074; A61B 2017/90
See application file for complete search history.

(56) References Cited

U.S. PATENT DOCUMENTS

| 5,112,337 A | 5/1992 | Palous et al. |
| 5,928,232 A | 7/1999 | Howland et al. |

(Continued)

FOREIGN PATENT DOCUMENTS

| CN | 206560458 U | 10/2017 |
| DE | 4219939 | 12/1993 |

(Continued)

OTHER PUBLICATIONS

Notice of Allowance received in connection with U.S. Appl. No. 16/956,253, dated Feb. 8, 2022, 10 pages.
(Continued)

*Primary Examiner* — Larry E Waggle, Jr.
(74) *Attorney, Agent, or Firm* — Meunier Carlin & Curfman LLC (57) ABSTRACT

A disposable guide device for spinal surgery comprises two tubular guide bodies extending along respective main axes between a proximal end and a distal end to guide a surgical operation on a vertebra of a patient, a plurality of support feet projecting laterally relative to each guide body, near said proximal end, each defining a contact area configured to abut on a side of the spinous process or on a lamina or facet or transverse process of the vertebra of the patient, in a mating configuration, at least one junction element extending between the guide bodies, starting from the respective distal ends, in order to space them from each other, wherein the guide bodies are oriented so that the proximal ends are more distant from each other with respect to the distal ends.

9 Claims, 6 Drawing Sheets

(51) Int. Cl.
  *A61B 17/84* (2006.01)
  *A61B 17/88* (2006.01)
  *A61B 17/70* (2006.01)
  *A61B 34/10* (2016.01)
  *A61B 17/00* (2006.01)
  *A61B 17/56* (2006.01)

(52) U.S. Cl.
  CPC .......... *A61B 17/8897* (2013.01); *A61B 17/90* (2021.08); *A61B 2017/0023* (2013.01); *A61B 2017/568* (2013.01); *A61B 2034/108* (2016.02)

(56) References Cited

U.S. PATENT DOCUMENTS

| | | | |
|---|---|---|---|
| 6,007,537 | A | 12/1999 | Burkinshaw et al. |
| 8,758,357 | B2 | 6/2014 | Frey |
| 8,870,889 | B2 | 10/2014 | Frey |
| 9,198,678 | B2 | 12/2015 | Frey et al. |
| 9,642,633 | B2 | 5/2017 | Frey et al. |
| 9,987,024 | B2 | 6/2018 | Frey et al. |
| 2002/0123668 | A1 | 9/2002 | Ritland |
| 2007/0066977 | A1 | 3/2007 | Assell et al. |
| 2008/0114370 | A1 | 5/2008 | Schoenefeld |
| 2012/0053590 | A1 | 3/2012 | Allen et al. |
| 2012/0130382 | A1 | 5/2012 | Iannotti et al. |
| 2012/0245587 | A1 | 9/2012 | Fang et al. |
| 2013/0053854 | A1 | 2/2013 | Schoenefeld et al. |
| 2013/0123850 | A1 | 5/2013 | Schoenefeld et al. |
| 2013/0218163 | A1 | 8/2013 | Frey |
| 2014/0074099 | A1 | 3/2014 | Vigneron et al. |
| 2014/0163565 | A1 | 6/2014 | Bollinger |
| 2014/0358152 | A1 | 12/2014 | Condino et al. |
| 2015/0320430 | A1 | 11/2015 | Kehres et al. |
| 2016/0030067 | A1* | 2/2016 | Frey .............. A61B 50/33 606/86 A |
| 2018/0042619 | A1 | 2/2018 | Frey et al. |
| 2018/0177512 | A1 | 6/2018 | Hogan et al. |
| 2021/0077119 | A1 | 3/2021 | Siccardi et al. |

FOREIGN PATENT DOCUMENTS

| | | |
|---|---|---|
| DE | 102016218965 A1 | 4/2018 |
| EP | 2502582 | 9/2012 |
| EP | 2749235 | 7/2014 |
| JP | 2015208566 A | 11/2015 |
| JP | 2016524506 | 8/2016 |
| TW | 200908927 | 3/2009 |
| TW | 201238556 | 10/2012 |
| WO | 9600049 | 1/1996 |
| WO | 2012/156466 A1 | 11/2012 |
| WO | 2013158521 | 10/2013 |
| WO | 2014070889 | 5/2014 |
| WO | 2014090908 | 6/2014 |
| WO | 20140197844 | 12/2014 |
| WO | 2016075581 | 5/2016 |
| WO | 2016075660 | 5/2016 |
| WO | 2018055494 | 3/2018 |
| WO | 2018055518 | 3/2018 |

OTHER PUBLICATIONS

International Search Report and Written Opinion issued for Application No. PCT/IB2017/055688. dated Nov. 16, 2017. 11 pages.
English Translation of Notice of Reasons of Refusal in JP 2019-536354, dated Feb. 10, 2020, 7 pages.
International Search Report and Written Opinion issued for Application No. PCT/IB2017/055588. dated Nov. 22, 2017. 13 pages.
English Translation of Notice of Reasons of Refusal in JP 2019-536348, dated Feb. 27, 2020, 14 pages.
International Search Report and Written Opinion for International Application No. PCT/IB2019/053765 dated Aug. 6, 2019. 15 pages.
International Search Report and Written Opinion for International Application No. PCT/IB2019/058162 dated Jan. 22, 2020, 16 pages.
Berry et al., Personalised image-based templates for intra-operative guidance, Proceedings of the Institution of Mechanical Engineers, Part H: Journal of Engineering in Medicine, vol. 219, pp. 111-118, 2004.
Brussel et al., Medical Image-Based Design of an Individualized Surgical Guide for Pedicle Screw Insertion, 18th Annual International Conference of the IEEE Engineering in Medicine and Biology Society, Amsterdam, pp. 225-226, 1996.
Lu et al., A novel computer-assisted drill guide template for placement of C2 laminar screws, Eur Spine J, vol. 18, pp. 1379-1385, 2009.
Lu et al., A Novel Patient-Specific Navigational Template for Cervical Pedicle Screw Placement. SPINE, vol. 34, No. 26, pp. E959-E964, 2009.
Lu et al., Rapid prototyping drill guide template for lumbar pedicle screw placement, Chinese Journal of Traumatology, vol. 12(3), pp. 171-177, 2009.
Popescu et al., Design and Rapid Manufacturing of Patient-Specific Spinal Surgical Guides: A Survey, Proceedings in Manufacturing Systems, vol. 7, Issue 2, pp. 115-120, 2012.
Radermacher, Klaus, Computer Assisted Orthopaedic Surgery with Individual Templates, Helmholtz-Institutefor Biomedical Engineering, 2 pages, 1997.
Ryken et al., Image-based drill templates for cervical pedicle screw placement, J Neurosurg Spine vol. 10, pp. 21-26, 2009.
International Search Report and Written Opinion, issued by the International Searching Authority (ISA/EP) in Application No. PCT/IB2018/060161 dated Apr. 5, 2019.
Office Action issued for U.S. Appl. No. 16/333,057, dated Jul. 30, 2020.
Office Action issued for U.S. Appl. No. 16/333,055, dated Dec. 8, 2020.
International Search Report and Written Opinion, issued by the International Searching Authority (ISA/EP) in Application No. PCT/IB2019/060161 dated Apr. 2, 2020.
International Search Report and Written Opinion, issued by the International Searching Authority (ISA/EP) in Application No. PCT/IB2018/060160 dated Apr. 5, 2019.
Office Action for U.S. Appl. No. 16/956,250, dated May 2, 2022.
Office Action issued for U.S. Appl. No. 16/956,253, dated Oct. 12, 2021.
Office Action issued for U.S. Appl. No. 17/281,900 dated Dec. 2, 2021.

* cited by examiner

DISPOSABLE GUIDE DEVICE FOR SPINAL SURGERY

CROSS REFERENCE TO RELATED APPLICATIONS

This application is a continuation of U.S. patent application Ser. No. 16/333,055, filed Mar. 13, 2019, which is a United States national phase application under 35 U.S.C. § 371 of International Application No. PCT/IB2017/055688, filed Sep. 20, 2017, which claims the benefit of priority to IT Patent Application No. 102016000095900, filed Sep. 23, 2016, the contents of which are incorporated herein by reference in their entireties.

FIELD OF INVENTION

The present invention relates to the technical field of orthopaedic surgery. More specifically, the invention relates to a disposable guide device for spinal surgery, used to help the surgeon to perform some delicate steps of surgical procedures, such as for example bone drills and cuts, which can be pre-operatively planned by computer-aided technologies.

The guide devices are disposable templates, which are typically customized, i.e. designed to match the bone anatomy derived from computed tomography images of a given patient.

Such devices are currently employed in several fields of orthopaedic surgery, including spinal surgery.

In this field, the guide devices are mainly employed to help the surgeon during pedicle screw insertion, so that the screw can be inserted according to a pre-planned optimal axis of the screw.

However, these devices may be used in spinal surgery for other purposes; for instance as cutting guides during PSO (pedicle substraction osteotomies), laminotomy or facectomies.

BACKGROUND

In general, known guide devices are provided with one or more guide bodies and one or more contact elements adapted to mate with the vertebrae of the patient in a stable and well defined configuration. In order to achieve this goal, large contact areas between the guide device and the patient's bone structure are required.

Therefore, before positioning the guide, the surgeon must wash the surrounding tissue away from a large area of the bone, and in some cases cut the ligaments. This often proves to be a difficult and costly task in terms of time, and can lead to complications and lengthening of the patient's hospitalization.

In addition, the residual tissue that cannot be removed by the surgeon can result in slipping and deviation of the guide device, which sometimes leads to incorrect or suboptimal positioning of the pedicle screws or bone resections.

But not only, the step of placing the guide in contact with the bone occurs after a preliminary step of inserting and positioning the guide, which is also made very difficult by the poor ergonomics of the device.

BRIEF SUMMARY

In view of the foregoing, the technical problem underlying the present invention is to provide a disposable guide device for spinal surgery, which can be easily handled and coupled in a stable and unique manner to the vertebrae of a patient.

The aforementioned technical problem is solved by means of a guide device for spinal surgery, according to claim 1.

In particular, the disposable guide device for spinal surgery comprises two tubular guide bodies extending along respective main axes from a proximal end to a distal end to guide a surgical operation on a vertebra of a patient.

In order to promote the stability of the device, a plurality of support feet is provided, which project laterally relative to each guide body, near said proximal end, each defining a contact area configured to abut on a respective portion of the vertebra; preferably, this portion is one side of the spinous process, a lamina, a facet, an articular process, or a transverse process of the patient's vertebra.

In addition, the device comprises at least one junction element extending between said guide bodies, starting from the respective distal ends, in order to space them from each other.

According to one aspect of the present invention, the guide bodies are oriented so that the proximal ends are more distant from each other with respect to the distal ends.

In certain embodiments, the junction element comprises at least one curved handle extending from both of the guide bodies, away from them, up to a top intermediate portion.

In order to optimize and facilitate the positioning/insertion steps, the handle is shaped so that a projection of its intermediate portion on each main axis of the guide bodies falls outside of the footprint of said guide bodies.

In other words, the handle's inclination and extension are such that the projection of its intermediate portion on each main axis has a distance from the proximal end greater than the distance between the proximal end and the distal end.

Advantageously, this facilitates the surgeon's gripping and manoeuvring of the device, particularly thanks to the arm that allows, with small movements of the hand, (relatively) large movements of the feet of the device.

In other embodiments, the junction element is preferably defined by at least one junction bridge between said two guide bodies provided with at least one central portion arranged astride a spinous process of the vertebra to be operated.

Preferably, the junction bridge is shaped so that its central portion is designed to pass over, with or without contact, the spinous process, thereby making the positioning of the device easier.

It should be noted that, in the preferred embodiments, the junction elements are two, i.e. the handle as well as the bridge.

Preferably, the bridge and the handle extend from the guide bodies away from each other. In other words, the bridge and the handle protrude from opposite sides of the guide bodies.

Advantageously, this configuration is particularly well adapted to the typical conformation of the cervical vertebrae, further facilitating a good positioning of the device.

BRIEF SUMMARY OF THE DRAWINGS

Further features and advantages of the patient-specific navigational guide according to the invention will become more apparent from the description, provided hereinbelow, of a number of embodiments described by way of non-limiting example with reference to the accompanying drawings, wherein.

FIGS. from 2 to 5 show several views of the disposable guide device of FIG. 1.

DETAILED DESCRIPTION

With reference to the accompanying figures, the numeral 1 indicates a guide device for spinal surgery according to the present invention.

In particular, the figures show a device specifically designed for surgery on a cervical vertebra 100.

As can be readily recognized in these figures, the guide device 1 comprises two tubular guide bodies 2.

These guide bodies 2 are connected to each other by means of a junction element 3 (or supporting frame).

More precisely, each guide body 2 extends along its main axis "A" between a distal end 2b and a proximal end 2a.

Note that the terms "distal" and "proximal", as used herein, refer to the position of an element (e.g. end) with respect to the vertebral body of the vertebra 100.

Therefore, each tubular guide body 2 houses an insertion duct 4 extending with substantial continuity between the distal end 2b and the proximal end 2a.

In other words, the duct 4 extends between a distal opening 4b, formed in the distal end 2b of the guide body 2, and a proximal opening 4a, formed in the proximal end 2a of the guide body 2.

It should be noted that the ducts 4 extend along the aforementioned main axes "A" of the guide bodies 2.

Therefore, the ducts 4 define respective insertion axes for two pedicle screws, which can be inserted in the vertebra 100 according to a pre-operatively planned angle.

Thus, the distal opening 4b corresponds to an access opening of the surgical instrument, while the proximal opening 4a faces the patient's vertebra 100, in the vicinity of the same.

Therefore, the diameter of the duct 4 is such as to allow the insertion of a Kirschner wire. In use, the Kirschner wire is implanted into the bone and, when the device 1 is removed, is used to guide a polyaxial screw, which runs along the wire in order to touch the bone at the predetermined point and be implanted. The inner diameter of the ducts 4 of the tubular guide members 2 can also be large enough to allow the passage of a polyaxial screw. Said inner diameter can be selected from 3-18 mm, 3-12 mm, 3-9 mm, 3-6 mm.

According to one aspect of the present invention, the guide bodies 2 are oriented so that the proximal ends 2a are more distant from each other with respect to the distal ends 2b.

In other words, the respective main axes "A" of the guide bodies 2 are oriented, starting from the distal ends 2b, away from each other.

Therefore, the guide device 1 according to the present invention preferably has a "diverging" configuration, in which the guide bodies 2 widen in the proximal region.

Advantageously, this simplifies the positioning of the device 1, thus reducing the space the surgeon needs for insertion.

As mentioned previously, a junction element 3 is provided between the two guide bodies 2.

Preferably, said at least one junction element 3 extends transversely to the two guide bodies 2 to place them in rigid connection.

More preferably, the junction element 3 is placed in the vicinity of the distal end 2b of the guide bodies 2.

This junction element 3 is therefore a (preferably non-straight) crossbar extending between the two guide bodies so as to space them.

Therefore, both the distal ends 2b and the proximal ends 2b of the guide bodies 2 are spaced from each other by a distance at least equal to a volume housing a spinous process 101 of the vertebra 100 to be operated.

According to a further aspect of the present invention, the junction element 3 comprises a curved handle 5 extending from both of the guide bodies 2, away from them, up to a top intermediate portion 5a.

In particular, the handle 5 is shaped so that a projection of its intermediate portion 5a on each main axis "A" of the guide bodies 2 falls outside of the footprint of said guide bodies.

Preferably, the handle 5 is thus a U- or V-shaped, in any case curved, element, such that the concavity defined by the top portion 5a faces the guide bodies 2.

Hence, the handle 5 comprises two end portions 5b extending from the distal ends 2b of the guide bodies 2 up to the intermediate portion 2a, preferably approaching each other.

Preferably, said handle 5 extends away from the guide bodies 2, with a predetermined inclination with respect to the main axis "A".

Figure 2:
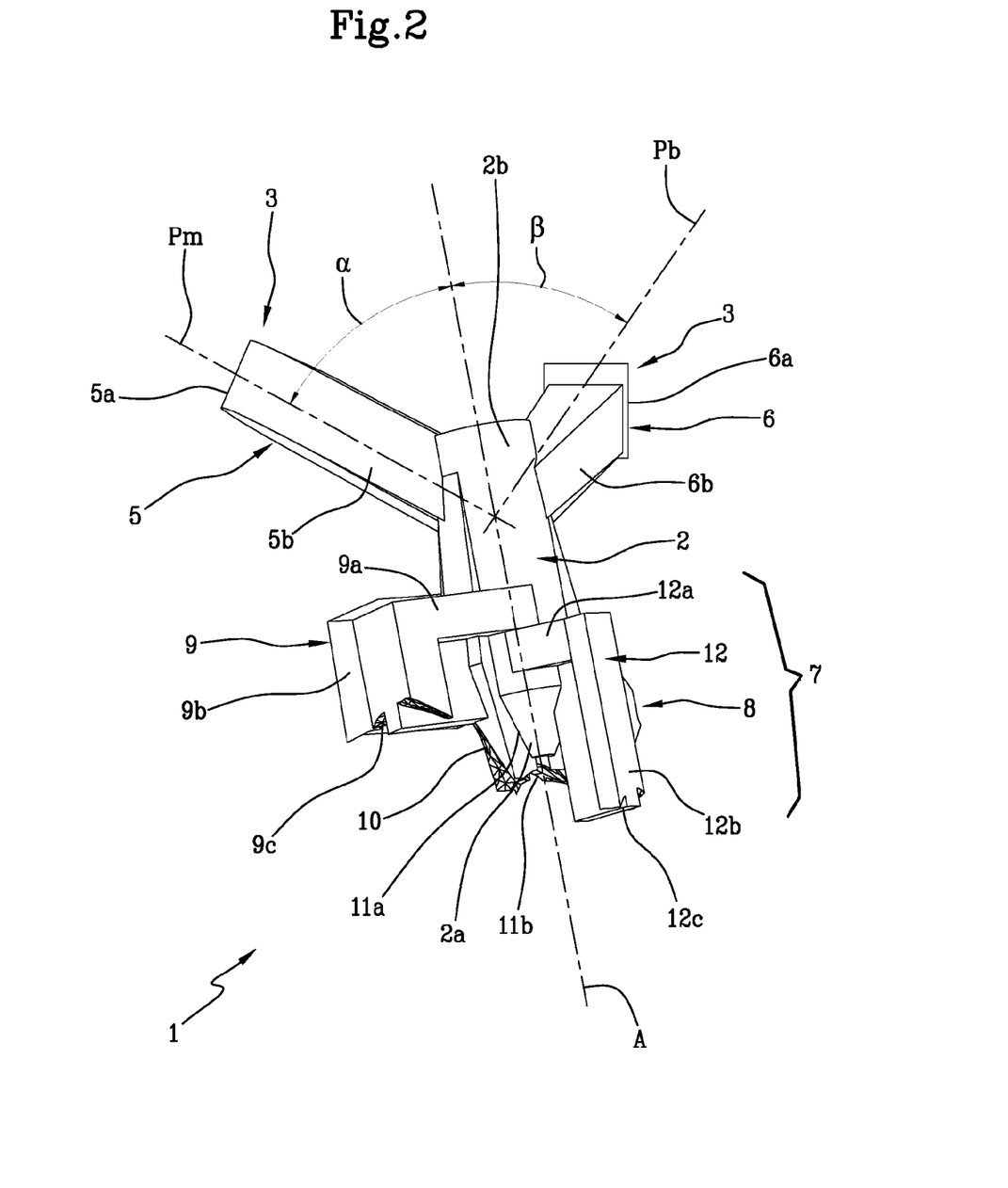

More precisely, with reference to a cross section plane "B" (FIG. 2) passing through the intermediate portion 5a of the handle 5, a projection of the main axis "A" on said section plane "B" defines a first angle α with a projection "Pm", on said section plane "B", of a median line of said handle 5.

The main axis "A" is preferably inclined with respect to the section plane by an angle γ comprised between 0° and 35°, more preferably between 10° and 20°.

As regards the first angle α, preferably, the first angle is comprised between 20° and 60°.

According to a further aspect of the present invention, the junction element 3 comprises at least one junction bridge 6 between said two guide bodies 2 provided with at least one central portion 6a designed to pass over the spinous process 101 of the vertebra 100 to be operated.

Figure 1:
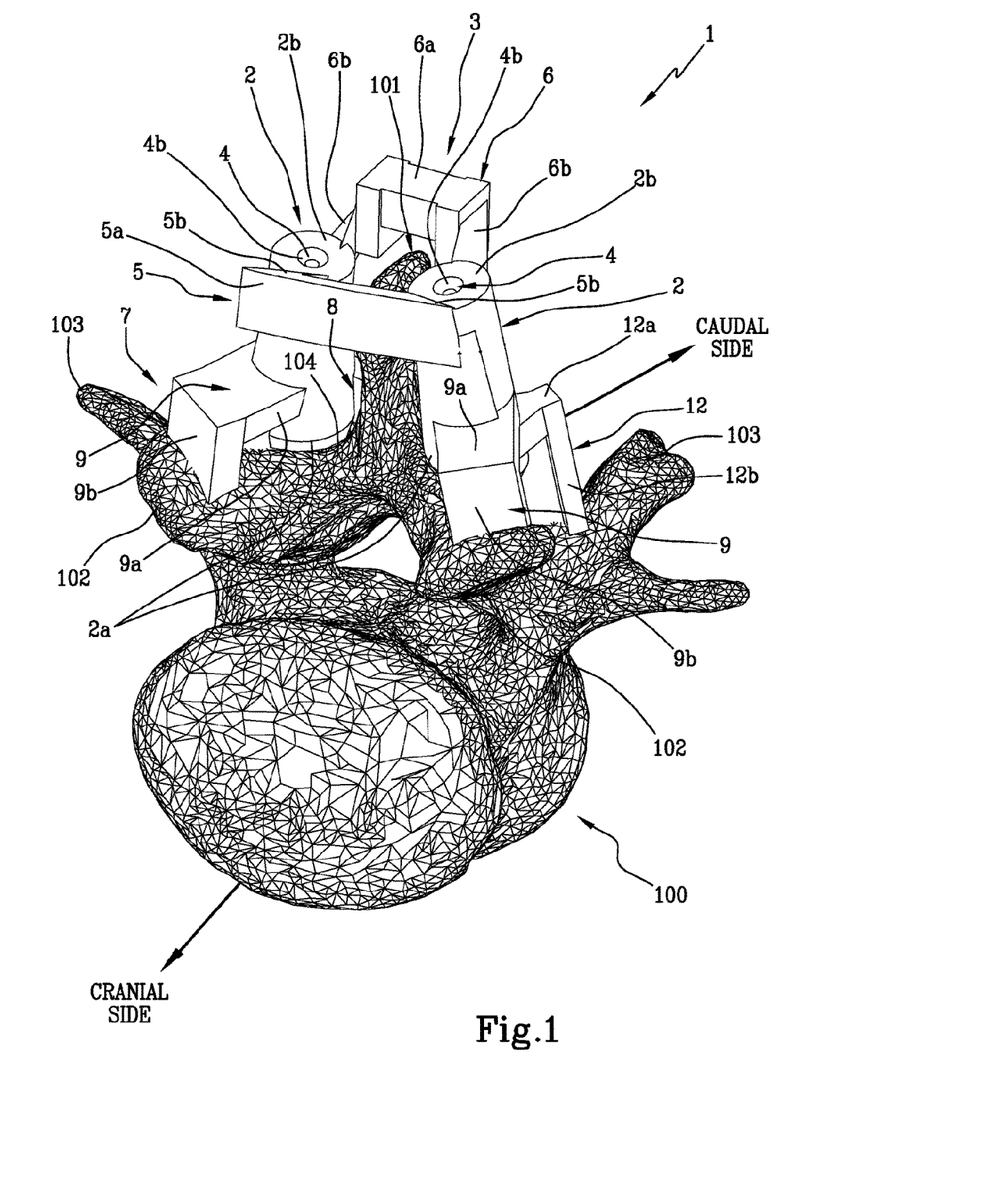
FIG. 1 shows a perspective view of a disposable guide device for spinal surgery according to the present invention, coupled to a cervical vertebra of the patient.
Figure 6:
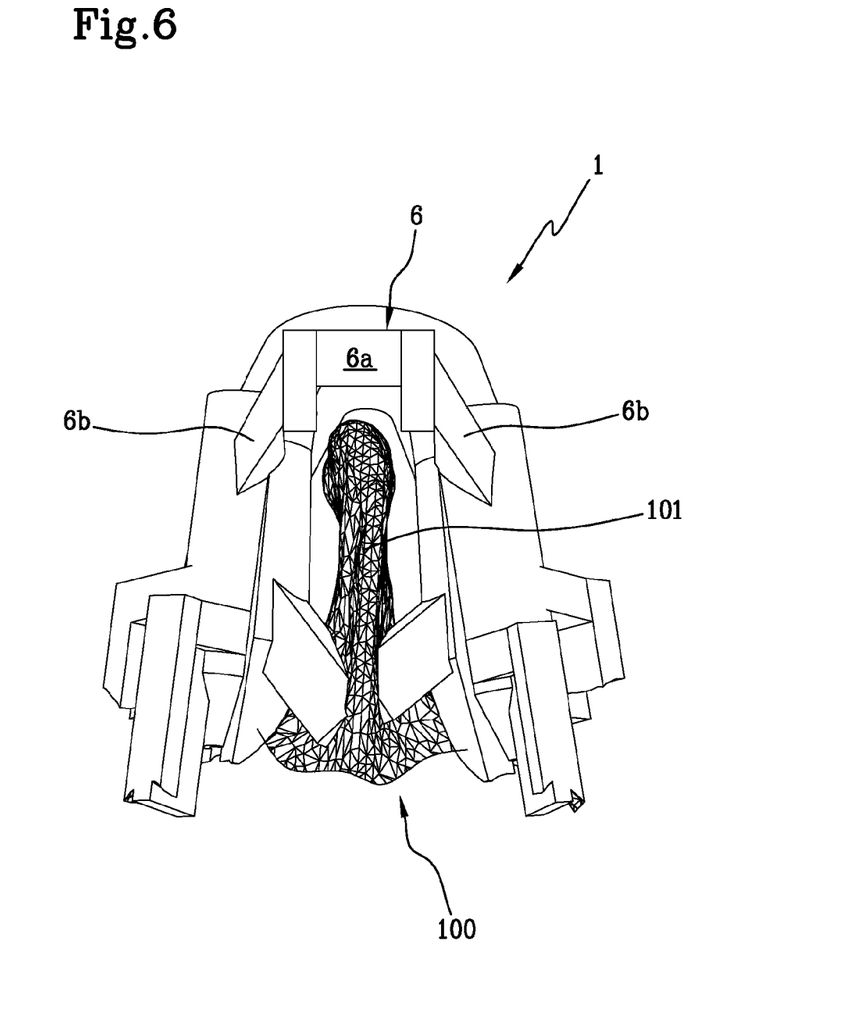
FIG. 6 shows an alternative embodiment of the guide device of FIGS. 1-5, wherein the spinous process is schematically shown in contact with the bridge.

More precisely, the central portion 6a can pass over the spinous process without contact (FIG. 1) or with contact, i.e. partially resting on it (FIG. 6).

The bridge 6 preferably comprises at least two arms 6b, each extending from a guide member 2; the central portion 6a connects the two arms 6b to each other. The arms 6b are preferably oriented in mutual approach.

Figure 3:
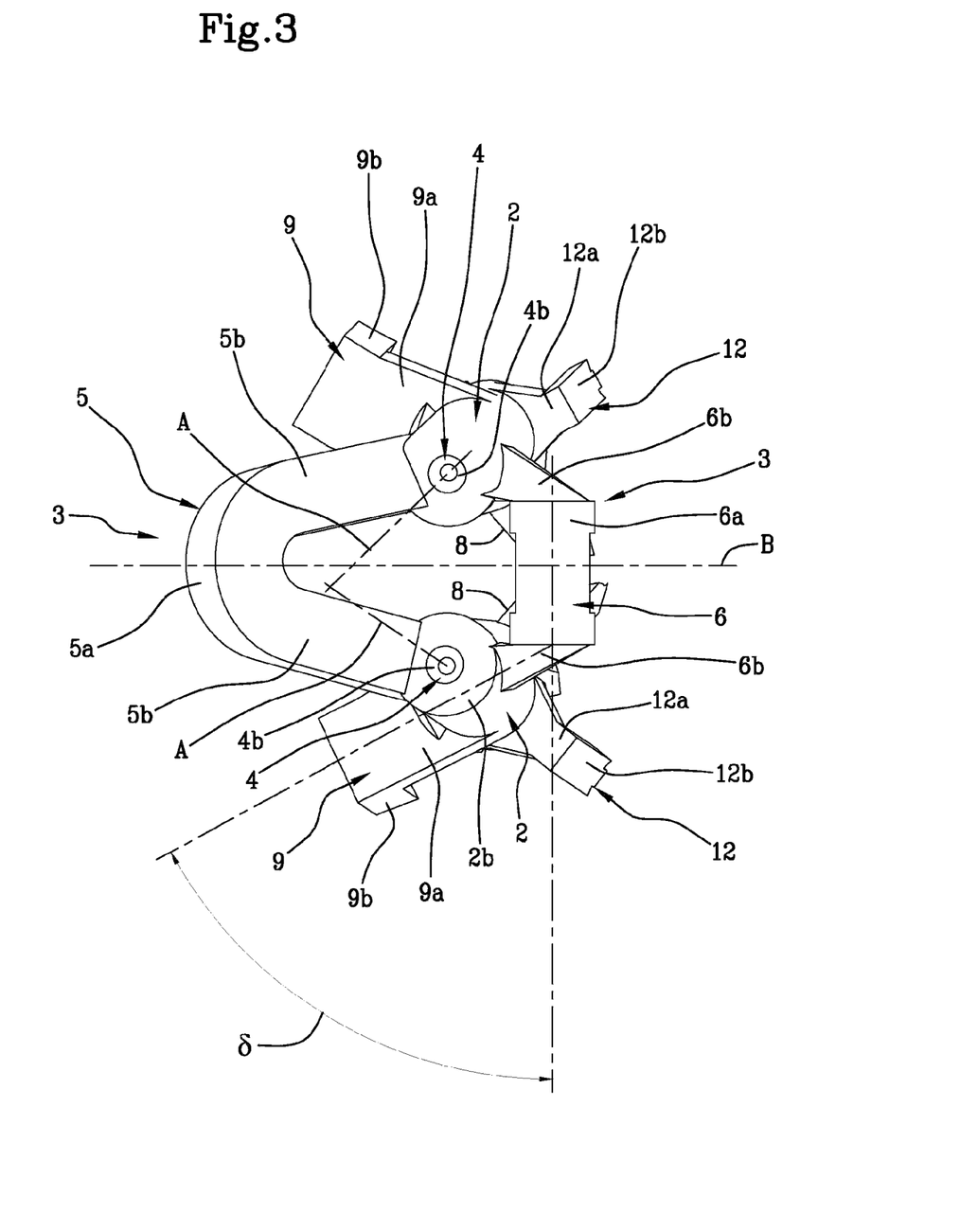
Figure 4:
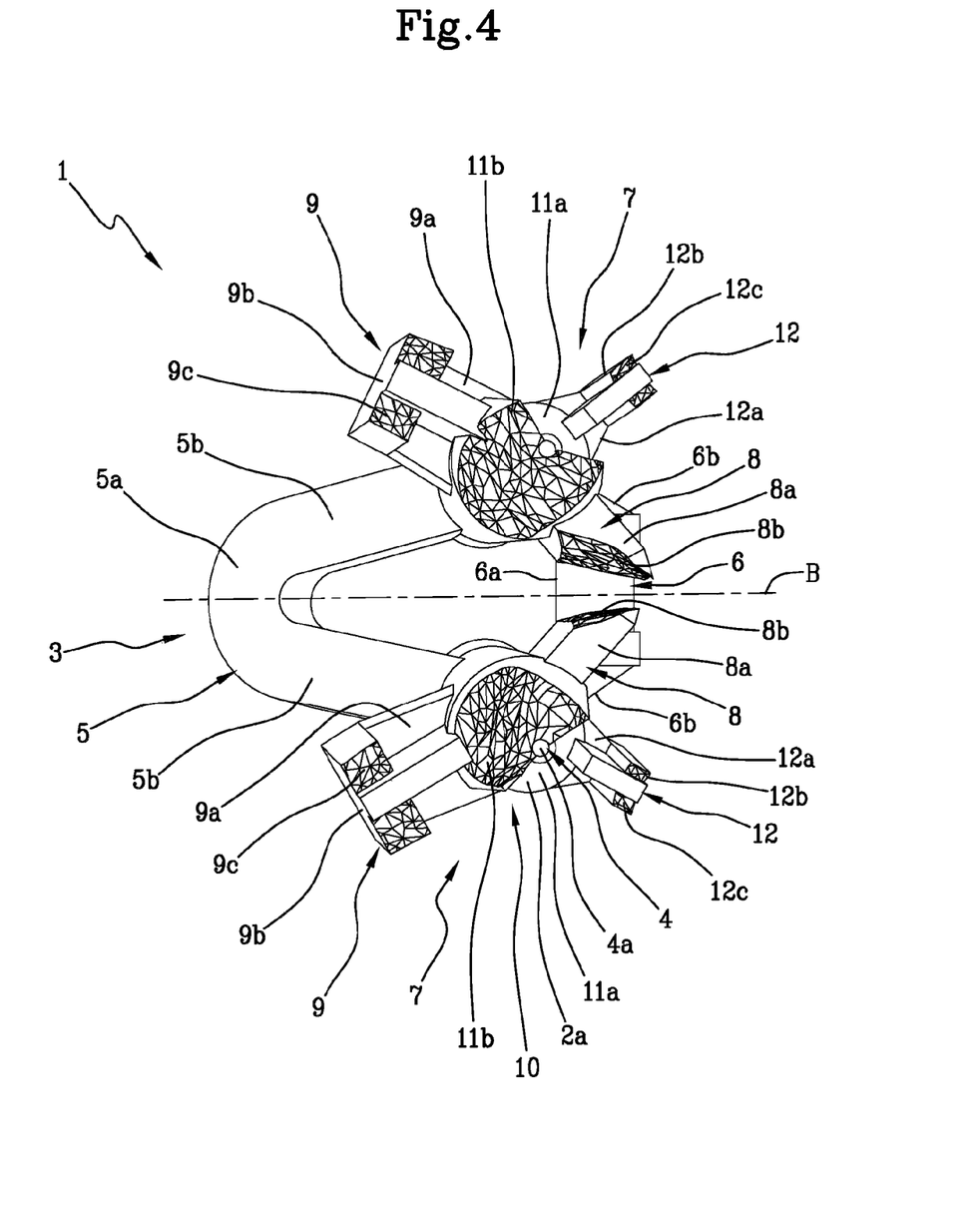
Figure 5:
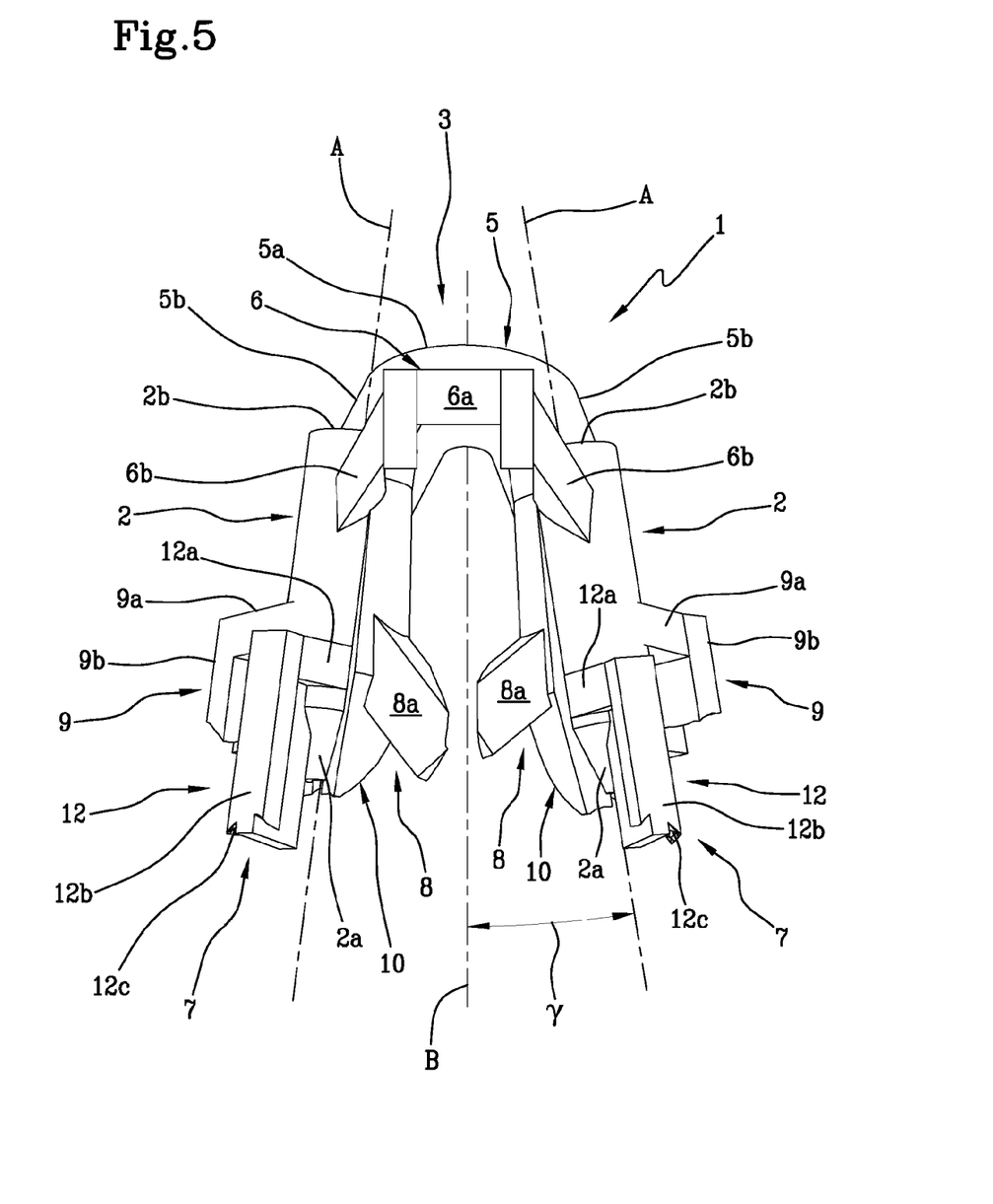

It should be noted that, preferably, the arms 6b have, in the plane of FIG. 3, an inclination with respect to a median axis of the central portion 6a comprised between 0° and 80°.

Therefore, the arms 6b have an inclination substantially comprised between approximately 0° and 80° with respect to a line joining the two ducts 4 (lying in a plane parallel to the plane of FIG. 3).

Advantageously, in this way, with the same entry point of the screw, i.e. keeping the position of the proximal opening 4a unchanged, by modifying the inclination of the arms 6b, the inclination of the ducts 4, i.e. of the guide bodies 2, can be varied correspondingly.

The central portion 6a of the bridge 6 is therefore designed to pass over the spinous process 101 of the vertebra 100 to be operated.

For this purpose, said central portion 6a has the shape of an inverted "U" internally defining a housing seat for the spinous process 101 of the vertebra 100.

Preferably, the central portion 6a of the bridge 6 comprises at least two lateral sides and a top wall defining said U-shape. The lateral sides are connected to the arms 6b.

In the preferred embodiment, the lateral sides and the top wall are substantially orthogonal and define a square configuration of the housing volume.

Advantageously, this makes the piece very simple and economical to manufacture.

It should be noted that the central portion 6a can take on various configurations depending on the application.

According to a first embodiment, shown in FIGS. 1-5, the housing seat is open in the cranial-caudal direction in order to prevent the patient's ligaments from being excised before placing the guide in the mating configuration (open profile).

As an alternative, not shown, the housing seat can be closed in the cranial-caudal direction by means of a septum or two septa that connect both lateral sides of the central portion 6a, forming, respectively, a semi-open or closed profile surrounding the spinous process 101, so as to ensure excellent stability to the operative guide 1.

With reference to a section plane "B" passing through the central portion of the bridge 6 (FIG. 2), a projection of the main axis "A" on said section plane "B" defines a second angle β with a projection "Pb", on said section plane "B", of a median line of said bridge 6.

Preferably, the second angle β is comprised between 20° and 60°.

In the preferred embodiment shown in FIGS. 1-5, the device 1 comprises both the handle 5 and the junction bridge 6, each defining a junction element 3.

Therefore, preferably, the device 1 comprises at least two junction elements 3.

Preferably, the bridge 6 and the handle 5 are arranged on opposite sides of the guide bodies 2.

In other words, the bridge 6 and the handle 5 extend from said guide bodies 2 away from each other.

Preferably, the bridge 6 and the handle 5 are shaped so that the first angle α is greater than the second angle β.

In this respect, it should be noted that the section plane "B" passes both through said intermediate portion 5a of the handle 5 and the central portion 6a of the bridge 6.

In particular, preferably, the sum of said first angle α and said second angle β is comprised between 45° and 100°.

Moreover, the handle 5 and the bridge 6 extend in such a way that the central portion 6a of the bridge 6 is proximal to the guide bodies 2 with respect to the intermediate portion 5a of the handle 5.

In other words, the handle 5 protrudes laterally relative to the guide bodies 2 in a more significant way compared to the bridge 6.

In addition, the handle 5 protrudes externally at the distal end 2b of the guide bodies 2 to a greater extent compared to the bridge.

In order to promote the stability of the device 1, it comprises a plurality of support feet 7, which project laterally relative to each guide body 2, near said proximal end 2a, each defining a contact area configured to abut on a respective portion of the vertebra 100.

Preferably, said portion is one side of the spinous process 101, a lamina 104, an articular process 102 or a transverse process 103 of the patient's vertebra 100.

Said feet 7 are pre-operatively planned by means of computer-aided design tools, on a three-dimensional model of the bone structure developed from a three-dimensional image (e.g., computed tomography image/magnetic resonance) of the patient. Therefore, each of the feet 7 (as well as the orientation of the guide bodies 2) is designed so that it uniquely matches the bone structure of the patient.

Preferably, the plurality of feet 7 comprises at least two feet for each guide body 2.

It should be noted that, preferably, the feet associated with each guide body are angularly spaced from one another so as to rest on the different portions of the vertebra in an "accurate" manner, thus reducing the overall contact surface and increasing the number of "isolated" contact points.

More precisely, each guide body 2 preferably comprises at least one first foot 8 defining a support element on one side of the spinous process 101 of the patient's vertebra 100.

Said first foot 8 preferably extends from a guide body 2 and is at least in part directed toward the other guide body 2.

Said first feet 8 are thus defined by protuberances 8a extending from a side wall of the guide bodies 2 (preferably, but not necessarily, approaching each other) and with a predetermined inclination with respect to the main axis "A".

Preferably, such protuberances 8a are substantially straight and inclined with respect to the guide body 2.

Each protuberance 8a ends with a contact face 8b shaped complementarily to the surface of the side of the spinous process 101 of the patient's vertebra 100.

More precisely, the first feet 8 extend along respective main directions defining acute angles with the portion of the main axis "A" included between a point of intersection with said main direction and the proximal end of the guide body 2.

In addition, each guide body 2 comprises at least one second foot 9 oriented away from the other guide body 2 and defining a support element on an articular process 102 (or transverse process 103) of the patient's vertebra 100.

These second feet 9 are substantially L-shaped.

More precisely, each second foot 9 preferably comprises a radial portion 9a and a contact portion 9b.

The radial portion 9a extends away from the respective guide body 2 along a direction substantially orthogonal to the main axis "A".

The contact portion 9b extends from a free end of the radial portion 9a transversely thereto; more precisely, such a contact portion extends from the radial portion 9a toward the proximal end 2a.

Said contact portion 9b ends, in turn, with an abutment face 9c shaped complementarily to the surface of the respective articular process 102 (or transverse process 103) of the patient's vertebra 100.

Advantageously, in this way, it is possible to obtain a particularly strong resting area even without the need for extensive resting surfaces.

In a preferred embodiment, the guide body 2 further comprises an enlarged portion 10 located near the proximal end 2a and defining a support base on the lamina 104 of the patient's vertebra 100.

In other words, the enlarged portion 10 is defined by an (at least partial) enlargement of the section in the vicinity of the proximal end 2a.

In this respect, it should be noted that, preferably, the proximal end 2a of each guide member 2 has at least one resting face shaped complementarily to the surface of the respective lamina 104 of the patient's vertebra 100.

More precisely, the proximal end 2a of the guide bodies 2 has a tapered half 11a, such as to facilitate the positioning and visualization by the surgeon, and a substantially flat half 11b, corresponding to said resting face of the enlarged portion 10.

Advantageously, this allows the stability of the device 1 to be maximized without increasing the encumbrance.

In certain embodiments, each guide body 2 is also provided with a further contact portion 12, also projecting laterally to the guide body 2 near the proximal end 2a and configured to abut on a transverse process 103 of the vertebra 100.

Preferably, said further contact portion 12 is also L-shaped, therefore provided with a radial portion 12a and a contact portion 12b directed toward the proximal end 2a of the guide body 2.

The contact portion 12b ends, in turn, with an abutment face 12c shaped complementarily to the surface of the respective transverse process 103 of the patient's vertebra 100.

The invention achieves the intended objects and attains important advantages.

In fact, the provision of a device with "diverging" guide bodies facilitates the positioning thereof, which is further facilitated by the presence of a handle protruding outside of the footprint of said guide bodies.

Moreover, the presence of numerous feet or contact portions angularly spaced in the vicinity of the proximal end of the guide bodies is even more advantageous in terms of stability.

The invention claimed is:

1. A disposable guide device for spinal surgery, comprising:
    two tubular guide bodies extending along respective main axes between a proximal end and a distal end to guide a surgical operation on a vertebra of a patient, and
    a plurality of support feet projecting laterally relative to each guide body, near said proximal end, each defining a contact area configured to abut on a side of a spinous process or on a lamina or facet or transverse process of the vertebra of the patient, in a mating configuration, wherein:
        the guide bodies are connected to each other by means of a junction element,
        the guide bodies are oriented so that the proximal ends are more distant from each other with respect to the distal ends, so that the respective main axes of the guide bodies are oriented, starting from the distal ends, away from each other,
        said junction element comprises at least one junction bridge between said two guide bodies provided with at least one central portion designed to pass over, with or without contact, a spinous process of the vertebra to be operated,
        each guide body comprises at least one first foot of said plurality of support feet defining a support element on one side of a spinous process of the patient's vertebra, wherein said first feet are thus defined by substantially straight protuberances each extending from a side wall of the relative guide body, with a predetermined inclination with respect to the main axis and directed towards the other guide body, wherein said predetermined inclination is defined by an acute angle delimited between the proximal end of the guide body and a free end of the first foot, wherein the acute angle is defined by an intersection between the main axis and an extension axis of the first foot,
    and wherein the disposable guide device is made in a single piece.

2. The guide device according to claim 1, wherein, with reference to a cross section plane passing through said central portion of the bridge, a projection of the main axis on said section plane defines a second angle with a projection, on said section plane, of a median line of said bridge.

3. The device according to claim 2, wherein said second angle is comprised between 20° and 60°.

4. The guide device according to claim 1, wherein said tubular guide bodies have respective tubular walls extending with continuity between said proximal end and said distal end.

5. The guide device according to claim 1, wherein each guide body comprises an enlarged portion near a proximal opening and defining a support base configured to abut the lamina of the vertebra of the patient.

6. The guide device according to claim 1, wherein the bridge comprises at least two arms, each extending from a guide member in mutual approach, and said central portion connecting said two arms to each other.

7. The guide device according to claim 6, wherein the arms have, with reference to a plane orthogonal to a cross section plane and transverse to said main axes, an inclination with respect to a median axis of the central portion comprised between 0° and 80°.

8. The guide device according to claim 1, wherein the central portion of the bridge comprises at least two lateral sides and a top wall defining a U-shape.

9. The guide device according to claim 8, wherein the lateral sides and the top wall are substantially orthogonal and define a square configuration.

* * * * *